· US010271824B2

United States Patent
Jalili

(10) Patent No.: US 10,271,824 B2
(45) Date of Patent: Apr. 30, 2019

(54) RECTUM GAS PASSAGE ANALYZER

(71) Applicant: Nooshin Jalili, Zanjan (IR)

(72) Inventor: Nooshin Jalili, Zanjan (IR)

( * ) Notice: Subject to any disclaimer, the term of this patent is extended or adjusted under 35 U.S.C. 154(b) by 0 days.

(21) Appl. No.: 15/907,750

(22) Filed: Feb. 28, 2018

(65) Prior Publication Data

US 2018/0185012 A1 Jul. 5, 2018

Related U.S. Application Data

(60) Provisional application No. 62/544,935, filed on Aug. 14, 2017.

(51) Int. Cl.
*A61B 10/00* (2006.01)

(52) U.S. Cl.
CPC ...... *A61B 10/00* (2013.01); *A61B 2010/0083* (2013.01)

(58) Field of Classification Search
CPC .................................................. A61B 10/00
USPC ........................................................ 600/562
See application file for complete search history.

(56) References Cited

U.S. PATENT DOCUMENTS

| | | | | |
|---|---|---|---|---|
| 2008/0051667 A1* | 2/2008 | Goldreich | .......... | A61B 5/02055 600/481 |
| 2009/0030386 A1* | 1/2009 | Kim | .................. | A61M 3/0241 604/328 |
| 2011/0184311 A1* | 7/2011 | Parihar | ............ | A61B 17/00234 600/562 |
| 2013/0061852 A1* | 3/2013 | Heinonen | ............. | A61M 16/20 128/204.21 |
| 2016/0374600 A1* | 12/2016 | Short | .................... | G06F 19/18 434/236 |
| 2017/0340264 A1* | 11/2017 | Gregersen | ........... | A61B 5/4255 |

* cited by examiner

*Primary Examiner* — Daniel L Cerioni
(74) *Attorney, Agent, or Firm* — Barry Choobin; Patent 360

(57) ABSTRACT

The various embodiments herein provide a device for analyzing a rectum gas discharge. The device comprises a central bag, a peripheral bag, and an electronic unit. The central bag comprises a gas inlet and a gas outlet on directionally opposite ends of a central bag surface. The peripheral bag is housed in a container and radially encapsulates the central bag. The electronic unit comprises a pressure sensor and a connector for further connecting a monitoring unit. The pressure sensor is attached over a surface of the peripheral bag. The central bag is attached to an anal canal of a patient and expands on ingestion of discharged rectal gas from the anal canal. The peripheral bag expands with the central bag resulting in activation of the pressure sensor to measure a gas collected in the central bag.

7 Claims, 3 Drawing Sheets

RECTUM GAS PASSAGE ANALYZER

BACKGROUND

Sponsorship Statement

The present invention is sponsored for international filing by Zanjan University of Medical Science.

Technical Field of Invention

The embodiments herein generally relate to a medical apparatus and particularly relate to a rectum gas passage analyser. The embodiments herein more particularly relate to a rectum gas analyser to record and analyse a digestive health of a person by analysing an amount of gas expelled through his rectum.

Description of Related Art

The rectum is the final straight portion of the large intestine in humans and some other mammals, and the gut in others. The adult human rectum is about 12 centimeters (4.7 in) long, and begins at the rectosigmoid junction, the end of the sigmoid colon, at the level of the third sacral vertebra or the sacral promontory. The rectum is responsible for storage and discharge of faeces and many time gases. The reduction or increase in a gas discharge through the rectum may lead to a plurality of diseases that may prove fatal if not properly diagnosed. An assessment of the volumetric discharge from the rectum to timely assess a rectal health is done in hospitals.

One of few prior art methods and systems for analysing the rectal gas discharge discloses a method for diagnosis of inflammatory conditions in the intestinal canal of humans, characterized in that NO (Nitric oxide) is measured in the lumen of the intestines. The NO level obtained is then compared with the level obtained for healthy individuals or with the level obtained for the same individual at another occasion. An increased level compared to the normal levels in the intestines of the healthy population is an indication of an inflammatory condition in the intestine.

However, such prior arts limit themselves to diagnosis of singular and neglect a generic gas analysis in volumetric manner. Such activities may prove inefficient in early detection of diseases like gastroesophageal reflux disease, intestinal obstruction etc.

Hence, there is no such device and system for an efficient analysis of rectal gas discharge. Also, there is no such system with automated method to detect an increase and decrease in a rectal gas discharge from a subject and generate an alert to caretaking authorities.

In the view of foregoing, there is a need for a device to solve the diagnosis problem of two types: a) a gas passage condition in patients' rectum and oesophagus:

The patients with LOC (low on consciousness) disorder or having confused state, cannot provide accurate information about their health condition. Generally, such patients suffer from an abdominal distension and an ileus diseases. In ileus disease, an acute abdomen needs an emergency surgery because the gas can't be removed from the digestive system. A secondary ileus caused by common electric disorders or other diseases or when digestive system has gas because of ventilator air leakage to intestine. In such diseases, the gas has to be removed from the digestive system. To diagnose the symptoms of ileus, the doctors check by radiography when the patient is conscious and a medical history is presented by the patient. But patients with LOC have limitations in presenting the medical history accurately. So, they have to be cured conservatively without diagnosing an exact problem. In such cases, the device for accurate gas analysis and system with record of rectal gas discharge provides near accurate information about patient's health.

b) Another problem includes an Irritable Bowel Syndrome (IBS) and various other diseases related to a gas disorder in the digestive system. Presently, there is no analyzer to record the exact volume and number of gas passage for these patients. The gas passage related information is presented by the patient himself but not in exact volumetric manner. Hence, the cure of such disease is done with minimal knowledge and known estimations. The need of a device with accurate gas discharge measurement adds a medical value in such cases.

An estimated volume of gas in digestive system is 200 cc. About 1000-1500 ml gas is expelled in from the rectum and the frequency of expelling is 10-20 times a day. In consideration of the rectal gas discharge, flatulence is a disease related to the IBS and can be diagnosed with the less procedure. The IBS is a common disease of digestive system affecting about 10-15% of population in the USA and about 11.5% of population in Europe. A person of younger age is more affected by the IBS in areas with cold temperature. One of the signs of the IBS is abdominal bloating and higher gas discharge. The IBS is primarily diagnosed by its symptom and a patient's declaration.

The above-mentioned shortcomings, disadvantages and problems are addressed herein, as detailed below.

SUMMARY OF THE INVENTION

The primary object of the embodiments herein is to provide a device and a system for an efficient analysis of rectal gas discharge.

Another object of the embodiments herein is to provide a system with automated method to detect an increase and decrease in a rectal gas discharge from a subject and generate an alert to caretaking authorities.

The various embodiments herein provide a device for analysing a rectum gas discharge. The device comprises a central bag, a peripheral bag, and an electronic unit. The central bag comprises a gas inlet and a gas outlet on directionally opposite ends of a central bag surface. The peripheral bag is housed in a container and radially encapsulates the central bag. The electronic unit comprises a pressure sensor and a connector for further connecting a monitoring unit. The pressure sensor is attached over a surface of the peripheral bag. The central bag is attached to an anal canal of a patient and expands on ingestion of discharged rectal gas from the anal canal. The peripheral bag expands with the central bag resulting in activation of the pressure sensor to measure a gas collected in the central bag.

According to one embodiment of the present invention, the pressure sensor is connected to the monitoring unit through the connector. The monitoring unit comprises a user interactive display, a central processing unit, a communication unit, and a memory unit.

According to one embodiment of the present invention, the gas enters the central bag through the gas inlet and after a measurement taken by the pressure sensor, the gas is expelled out through the gas outlet without coming in contact with the peripheral bag.

According to one embodiment of the present invention, the memory unit saves an expelled gas data sent from the pressure sensor and transmits the collected data over a period to the central processing unit to analyse and map with a reference data. The reference data is a data pertaining gas expelled analysis in a health human.

According to one embodiment of the present invention, the communication unit transmits the analytical data created by the central processing unit to a nearest health personnel in an event of continuous mismatch between the expelled gas data of the patient and reference data.

According to one embodiment of the present invention, the central bag and the peripheral bag are made up of an inert elastomeric material.

According to one embodiment of the present invention, the gas outlet is one way valve controlled by the pressure sensor. The pressure sensor is connected to the gas outlet through an actuator. The actuator opens the gas outlet after completion of a measurement of the expelled gas by the pressure sensor.

According to one embodiment of the present invention, the gas inlet is one way valve to only allow an ingestion of the expelled rectal gas.

According to one embodiment of the present invention, the device further comprises a gas composition analyser connected to the gas outlet and the electronic unit to analyse a presence different gaseous contents in the expelled rectal gas.

These and other aspects of the embodiments herein will be better appreciated and understood when considered in conjunction with the following description and the accompanied drawings. It should be understood, however, that the following descriptions, while indicating preferred embodiments and numerous specific details thereof, are given by way of illustration and not of limitation. Many changes and modifications may be made within the scope of the embodiments herein without departing from the spirit thereof, and the embodiments herein include all such modifications.

BRIEF DESCRIPTION OF THE DRAWINGS

The other objects, features and advantages will occur to those skilled in the art from the following description of the preferred embodiment and the accompanied drawings in which.

DETAILED DESCRIPTION OF THE DRAWINGS

In the following detailed description, a reference is made to the accompanied drawings that form a part hereof, and in which the specific embodiments that may be practiced is shown by way of illustration. The embodiments are described in sufficient detail to enable those skilled in the art to practice the embodiments and it is to be understood that the logical, mechanical and other changes may be made without departing from the scope of the embodiments. The following detailed description is therefore not to be taken in a limiting sense.

Figure 1A:
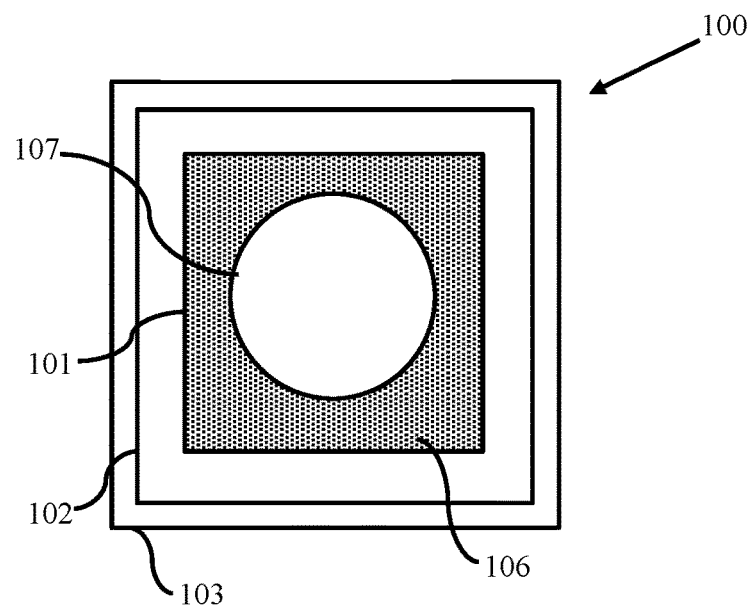
FIGS. 1a and 1b illustrates a top view and a side view respectively of a device for analysing a rectal gas discharge, according to one embodiment herein.
Figure 1B:
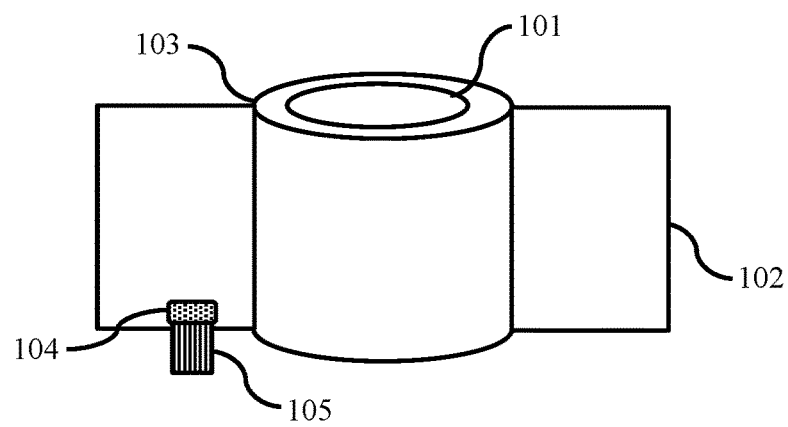

With respect to FIGS. 1a and 1b, a device 100 for analysing a rectum gas discharge is illustrated. The device 100 comprises a central bag 101, a peripheral bag 102 and an electronic unit. The central bag 101 comprises a gas inlet 107 and a gas outlet on directionally opposite ends of a central bag surface. The peripheral bag 102 is housed in a container 103 and radially encapsulates the central bag 101. The central bag 101 and the peripheral bag 102 are pressure sensitive in nature and expands even with insertion of small volume of gas or a gas expelled with low pressure. The electronic unit comprises a pressure sensor 104 and a connector 105 for further connecting a monitoring unit. The pressure sensor 104 is connected to the peripheral bag 102. The central bag 101 is attached to an anal canal of a patient and expands on ingestion of discharged rectal gas from the anal canal. The central bag uses a hollow and flexible pipe 106 to be inserted or connected to the anal canal. The peripheral bag 102 expands with the central bag 101 resulting in activation of the pressure sensor 104 to measure a gas collected in the central bag.

According to one embodiment of the present invention, the pressure sensor is connected to the monitoring unit through the connector. The monitoring unit comprises a user interactive display (UID), a central processing unit, a communication unit, and a memory unit.

According to one embodiment of the present invention, the gas enters the central bag through the gas inlet and after a measurement taken by the pressure sensor the gas is expelled out through the gas outlet without coming in contact with the peripheral bag.

According to one embodiment of the present invention, the memory unit saves an expelled gas data sent from the pressure sensor and transmits the collected data over a period to the central processing unit to analyse and map with a reference data. The reference data is a data pertaining gas expelled analysis in a health human.

According to one embodiment of the present invention, the communication unit transmits the analytical data created by the central processing unit to a nearest health personnel in an event of continuous mismatch between the expelled gas data of the patient and reference data.

According to one embodiment of the present invention, the central bag and the peripheral bag are made up of an inert elastomeric material.

According to one embodiment of the present invention, the gas outlet is one way valve controlled by the pressure sensor. The pressure sensor is connected to the gas outlet through an actuator. The actuator opens the gas outlet after completion of a measurement of the expelled gas by the pressure sensor.

According to one embodiment of the present invention, the gas inlet is one way valve to only allow an ingestion of the expelled rectal gas.

According to one embodiment of the present invention, the device further comprises a gas composition analyser connected to the gas outlet and the electronic unit to analyse a presence different gaseous contents in the expelled rectal gas.

Figure 2A:
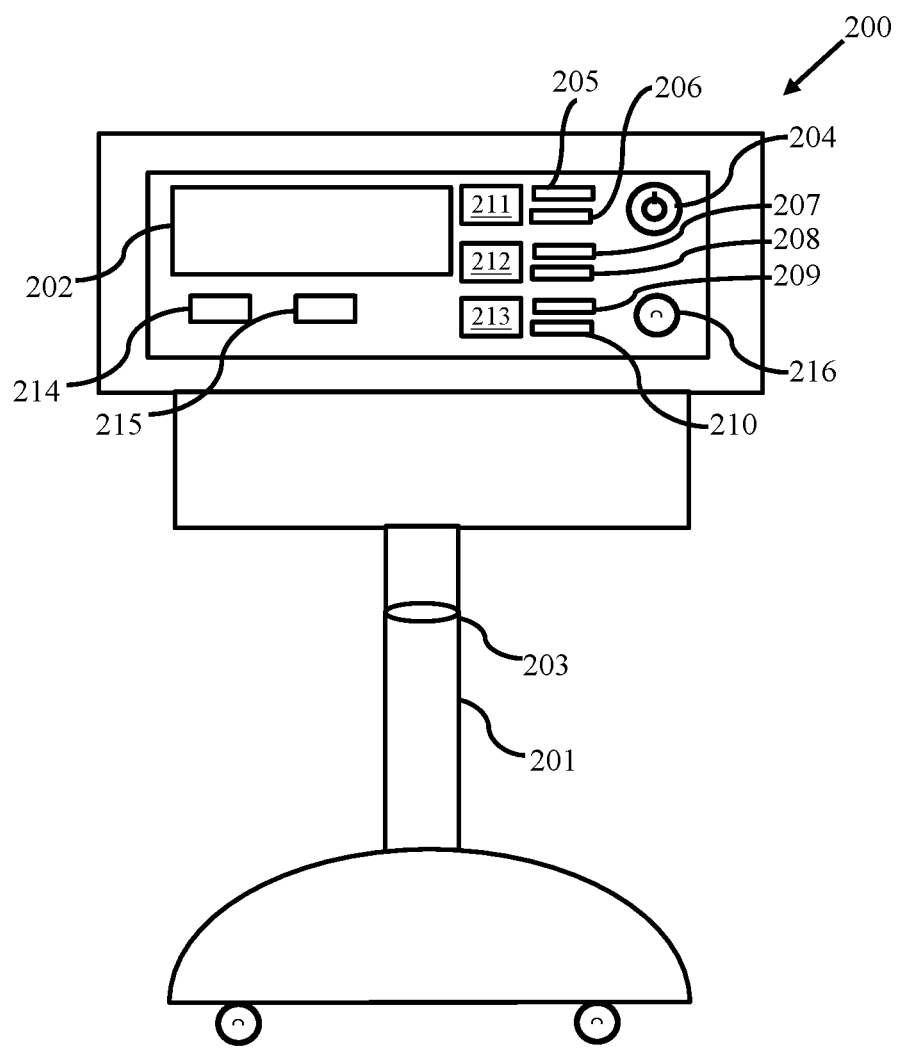
FIG. 2a illustrates a monitoring unit connected with rectal gas analyser device, according to one embodiment herein.

With respect to FIG. 2a, the monitoring unit 200 is a moveable unit comprising a base stand 201 and the UID 202 connected to the base stand through a flexible neck 203. The flexible neck 203 allows the UID 202 to flex in multiple directions with respect to the base stand. The UID 202 is touch responsive in nature and comprises a power button 204, a monitor to show graphical data for rate and volume of expelled gas 214, an alarm button 215, a confirmation button 216 and at least one mini window for each parameter. The parameter comprises a rate of gas expulsion during at least last 24 hours 205, a frequency of gas expulsion during at least last hour 206, a volume of expelled gas during at least last hour 207, a volume of expelled gas during at least last 24 hours 208, a pressure of expelled gas during at least last hour 209 and a volume of expelled gas during at least last 24 hours 210. The rate, volume and pressure parameters appears on the UID 202 by pressing a rate button 211, a volume button 212 and a pressure button 213 respectively. The graphical data on the monitor 214 is shown after pressing a monitor button 217 as illustrated in FIGS. 2c and 2d. The confirmation button 216 is selected to accept and store the data shown on the UID in the memory unit.

Figure 2B:
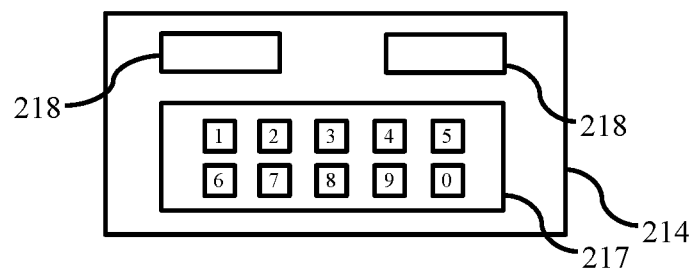
FIG. 2b illustrates a display page on the UID on selection of an alarm button, according to one embodiment herein.
Figure 2C:
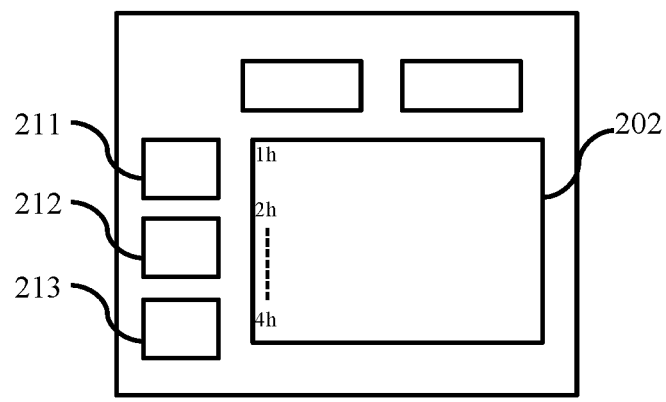
FIGS. 2c and 2d illustrates display pages on the UID on selection of a monitor button, according to one embodiment herein.
Figure 2D:
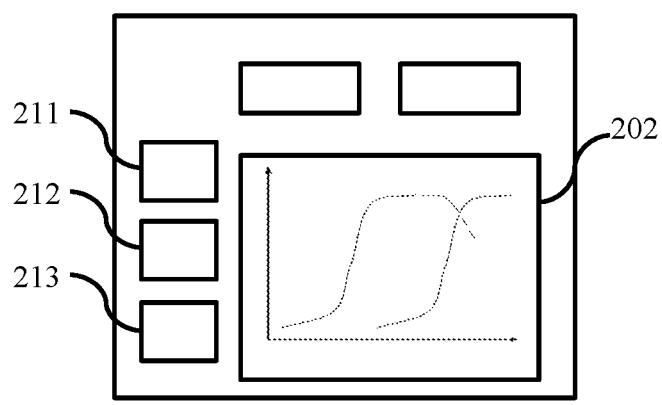

With respect FIG. 2b, on selection of an alarm button 215, a key pad 217 and an alert window 218 appears on the monitor 214. The patient or a care taker is enabled to enter a preferred rate and volume of expelled gas. If the measured rate and volume of expelled gas from the patient falls within the limits of the entered data, then the colour of the alert window turns green, otherwise the alert window turns red in colour. The activation of red colour activates the communication unit to an alert notification along with the measured data to a nearest health personnel.

According to one embodiment herein, the limit of the entered data is taken as a ±10% range of the entered data.

The present rectum gas analyser device is portable in nature and easy to use. The device allows a continuous monitoring of the expelled gas and can also measure contents of the expelled gas to efficiently determine a health of the digestive system. The data collected by the present device allows an accurate determination of cause of malfunctioning of the digestive system and diagnose the same.

It is to be understood that the phraseology or terminology employed herein is for the purpose of description and not of limitation. Therefore, while the embodiments herein have been described in terms of preferred embodiments, those skilled in the art will recognize that the embodiments herein can be practiced with modification within the spirit and scope of the claims.

I claim:

1. A device for analyzing a rectum gas discharge comprising:
    a central bag, wherein the central bag comprises a gas inlet and a gas outlet on directionally opposite ends of a central bag surface;
    a peripheral bag, wherein the peripheral bag is housed in a container and radially encapsulates the central bag;
    an electronic unit, wherein the electronic unit comprises a pressure sensor and a connector for further connecting a monitoring unit, wherein the pressure sensor is attached over a surface of the peripheral bag;
    wherein said device includes a hollow and flexible pipe that is used by the central bag to attach to the anal canal;
    wherein, the central bag is attached to an anal canal of a patient and expands on ingestion of discharged rectal gas from the anal canal, wherein the peripheral bag expands with the central bag resulting in activation of the pressure sensor to measure a gas collected in the central bag;
    wherein the pressure sensor is connected to the monitoring unit through the connector, wherein the monitoring unit comprises a user interactive display, a central processing unit, a communication unit, and a memory unit; and
    wherein the memory unit saves an expelled gas data sent from the pressure sensor and transmits the collected data over a period to the central processing unit to analyse and map with a reference data, wherein the reference data is a data pertaining gas expelled analysis in a health human.

2. The device according to claim 1, wherein the gas enters the central bag through the gas inlet and after a measurement taken by the pressure sensor the gas is expelled out through the gas outlet without coming in contact with the peripheral bag.

3. The device according to claim 1, wherein the communication unit transmits the analytical data created by the central processing unit to a nearest health personnel in an event of continuous mismatch between the expelled gas data of the patient and reference data.

4. The device according to claim 1, wherein the central bag and the peripheral bag are made up of an inert elastomeric material.

5. The device according to claim 1, wherein the gas outlet is one way valve controlled by the pressure sensor, wherein the pressure sensor is connected to the gas outlet through an actuator, wherein the actuator opens the gas outlet after completion of a measurement of the expelled gas by the pressure sensor.

6. The device according to claim 1, wherein the gas inlet is one way valve to only allow an ingestion of the expelled rectal gas.

7. The device according to claim 1 further comprises a gas composition analyser connected to the gas outlet and the electronic unit to analyse a presence different gaseous contents in the expelled rectal gas.

* * * * *